United States Patent [19]

Corrigan et al.

[11] Patent Number: 6,080,853
[45] Date of Patent: Jun. 27, 2000

[54] POLYOL POLYESTER SYNTHESIS

[75] Inventors: Patrick Joseph Corrigan, Cincinnati; Roger Stephen Berger, Fairfield, both of Ohio

[73] Assignee: The Procter & Gamble Company, Cincinnati, Ohio

[21] Appl. No.: 08/976,459

[22] Filed: Nov. 21, 1997

Related U.S. Application Data

[63] Continuation of application No. 08/694,137, Aug. 8, 1996, abandoned.

[51] Int. Cl.$^7$ .............................. C07H 13/06; C07C 67/03
[52] U.S. Cl. ............................................. 536/119; 554/168
[58] Field of Search .............................. 536/119; 554/168

[56] References Cited

U.S. PATENT DOCUMENTS

| | | | |
|---|---|---|---|
| 3,251,827 | 5/1966 | Schnell et al. | 536/119 |
| 3,963,699 | 6/1976 | Rizzi et al. | 536/119 |
| 4,032,702 | 6/1977 | James | 536/119 |
| 4,298,730 | 11/1981 | Galleymore et al. | 536/119 |
| 4,334,061 | 6/1982 | Bossier, III | 536/119 |
| 4,518,772 | 5/1985 | Volpenhein | 536/119 |
| 4,931,552 | 6/1990 | Gibson et al. | 536/119 |
| 4,996,309 | 2/1991 | Matsumoto et al. | 536/119 |

FOREIGN PATENT DOCUMENTS

| | | |
|---|---|---|
| 49-43694 | 10/1975 | Japan . |
| 1250204 | 10/1971 | United Kingdom . |
| 92/04360 | 3/1992 | WIPO . |
| 92/04361 | 3/1992 | WIPO . |

OTHER PUBLICATIONS

"McGraw–Hill Dictionary of Scientific and Technical Terms" Third Edition, p. 1337, McGraw–Hill Book Company (1984).

"Kirk–Othmer Encyclopedia of Chemical Technology", Third Edition, vol. 19, pp. 880–883, John Wiley & Sons (1982).

"A Solvent–free Synthesis of Sucrose Polyesters", *Journal of the American Oil Chemists' Society*, vol. 55, pp. 398–401 (Apr., 1978).

"Preparation of Sucrose Esters by Interesterification", *Journal of The American Oil Chemists' Society*, vol. 47, pp. 56–60 (Feb., 1970).

*Primary Examiner*—Richard L. Raymond
*Attorney, Agent, or Firm*—Karen F. Clark; Jacobus C. Rasser

[57] ABSTRACT

Polyol polyesters useful as nondigestible fat substitutes are prepared by improved heterogeneous interesterification processes between fatty acid esters of easily removable alcohol and polyol wherein the particle size of the polyol is reduced to less than 100 microns, and when the degree esterification of the polyol is between about 15% and no more than 75% substantially all of the unreacted polyol is removed. In the initial or early stages of the reaction, reaction conditions are adjusted to maintain a sufficient level of lower partial fatty acids to act as an emulsifier. The initial catalyst level is from about 0.001 to about 0.5 catalyst per mole of catalyst.

24 Claims, No Drawings

POLYOL POLYESTER SYNTHESIS

This is a continuation of application Ser. No. 08/694,137, filed on Aug. 8, 1996 now abandoned.

TECHNICAL FIELD

This invention relates to improved synthesis of higher polyol fatty acid polyesters, especially sucrose polyesters, and more especially via transesterification reactions that do not use a solvent to form a homogeneous reaction mix, and preferably, and more specifically to a continuous process that is capable of making said polyesters more efficiently and/or making said polyesters of improved quality.

BACKGROUND OF THE INVENTION

Processes for preparing polyol fatty acid polyesters, including processes that utilize solvent-free transesterification reactions, have been described in U.S. Pat. No. : 3,963,699, Rizzi et al., issued Jun. 15, 1976; U.S. Pat. No. 4,517,360, Volpenhein, issued May 14, 1985; and U.S. Pat. No. 4,518,772, Volpenhein, issued May 21, 1985. Additional patents describing processes for preparing lower and higher esters of polyols include U.S. Pat. Nos.: U.S. Pat. No. 2,893,990, Hass et al., issued Jul. 7, 1959; U.S. Pat. No. 3,251,827, Schnell et al., issued May 17, 1966, which discloses that the particle size of the sugar should be kept small to avoid formation of higher esters; U.S. Pat. No. 3,558,597, Brachel et al., issued Jan. 26, 1971; U.S. Pat. No. 3,644,333, Osipow et al., issued Feb. 22, 1972; U.S. Pat. No. 3,792,041, Yamagishi et al., issued Feb. 12, 1974, which discloses making a solution of sucrose and fatty acid soap in water and adding the fatty acid ester and catalyst before elevating the temperature to drive off the water, U.S. Pat. No. 4,032,702, James, issued Jun. 28, 1977, which discloses using lower esters of sucrose as emulsifiers in the preparation of lower esters and the use of soap as a catalyst for such reactions; U.S. Pat. No. 4,298,730, Galleymore et al., issued Nov. 3, 1981, which also discloses the use of soap as an emulsifier and catalyst; U.S. Pat. No. 4,334,061, Bossier et al., issued Jun. 8, 1982, which discloses the use of a water washing step to purify the polyol polyester and incidentally discloses the use of inert gas sparging to remove lower alcohol from the reaction between sucrose and lower alkyl ester of fatty acid to speed the reaction and the removal of unreacted sucrose from an initial stage of a batch reaction for no indicated reason; and U.S. Pat. No. 4,877,871, Klemann et al., issued Oct. 31, 1989.

Many of the above patents teach processes that use a solvent to assist in the formation of a homogeneous reaction mixture. However, the presence of the solvent is not desirable since it must then be removed. Also, many of the above processes primarily relate to the preparation of lower esters, containing one or two ester groups, that are desirable for use as surfactants. The present process primarily relates to an improved and highly effective method of preparing of polyol polyesters that have high degrees of esterification, preferably polyesters that are more than about 50% esterified, i.e., at least about 50% of the total number of available hydroxy groups on the polyol are esterified with a fatty acyl radical.

The presence of unreacted polyol in stage two has been surprisingly found to be a key detriment to the reaction rate and final conversion of the polyol to greater than 85% degree of esterification. The removal of essentially all of the polyol (sucrose) before stage 2 greatly facilitates preparation of octa esters. In order to have a better commercial process for preparing highly esterified polyols, it is desirable to have a fast continuous process.

SUMMARY OF THE INVENTION

The present invention relates to improved, preferably continuous, processes for preparing highly esterified polyol fatty acid polyester by interesterifing (a) polyol containing more than about four esterifiable hydroxy groups and (b) fatty acid ester of easily removable alcohol, in a heterogeneous reaction mixture, e.g., in the absence of any substantial amount of unreactive solvent, wherein:

(1) The polyol used to prepare the said polyester is preferably particulate solid, preferably sucrose, that has had its particle size reduced by mechanical size reduction, e.g., grinding, to a particle size of less than about 100 microns, preferably less than about 50 microns, and more preferably less than about 10 microns;

(2) The process is a continuous process in which the initial catalyst level is from about 0.01 to about 0.5 mole of catalyst per mole of polyol, preferably from about 0.01 to about 0.1 mole of catalyst per mole of polyol;

(3) An emulsifier can be used but is not essential. If soap is used, the initial level of soap emulsifier in the first stage of the reaction is from about 0.001 to about 0.6, preferably from about 0.05 to about 0.1 moles per mole of polyol;

(4) After the degree of esterification is greater than about 60% and at least some of any soap emulsifier that is present is insoluble in the reaction mixture, removing the insoluble soap, and any other large particles, e.g., by filtration, preferably in a continuous process;

(5) Any unreacted polyol, e.g., sucrose, and any catalyst having particle sizes above about 1 micron are removed, e.g., by filtration, before the degree of esterification reaches about 75%, and preferably after it has reached 35%, more preferably after 45%, and before any substantial amount of soap emulsifier present has become insoluble in the reaction mixture. Preferably in a continuous process, the unreacted polyol at this stage should be less than 0.5%.

(6) The initial stage of the reaction, and especially in a continuous process that uses multiple reaction vessels, is carried out under conditions, e.g., of backmixing, to maintain a level of lower partial esters of said polyol in an emulsifying amount, typically corresponding to an average degree of esterification of the polyol of from about 10% to about 75%, preferably from about 35% to about 40%. Backmixing is preferred, either within the reaction vessel, as a result of the hydrodynamics that are characteristic of a backmix reactor, or by recycling a portion of the reaction mixture, or, more preferably, by using two backmix reactors in series for the initial stage, with the product of the first reactor in the initial stage having a degree of esterification of from about 10% to about 30%, and the product of the second reactor having a degree of esterification of from about 30% to about 50%; and (7) The final stage, or stages, of the reaction are carried out under conditions that at least approach plug-flow, after the degree of esterification of said polyol has reached at least about 50% to achieve a final degree of esterification of at least about 85%, preferably at least about 95%; of the hydroxy groups esterified.

DETAILED DESCRIPTION OF THE INVENTION

The Polyol

As used herein, the term "polyol" is intended to include any linear, cyclic, or aromatic compound containing at least four free esterifiable hydroxyl groups. In practicing the process disclosed herein, sucrose is the most highly preferred polyol. If sucrose is not used, then the selection of a suitable alternative polyol is simply a matter of choice. For example, suitable polyols can be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates and nontoxic glycols are preferred polyols. Monosaccharides suitable for use herein include, for example, mannose, galactose, arabinose, xylose, ribose, fructose, sorbose, and erythrulose. Oligosaccharides suitable for use herein include, for example, maltose, cellobiose, lactose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol. It is desirable that the aldehyde groups in the polyol be changed to alcohol groups or reacted with alcohol groups to form ether linkages, including sorbitans, alkoxylabid polyols such as ethoxylated glycine or exthexylated polyglycerol or sorbitans can also be used. Polyglycerol is also a suitable polyol for use herein.

Particularly preferred classes of materials suitable for use herein include the monosaccharides, the disaccharides and sugar alcohols. Preferred carbohydrates and sugar alcohols include xylitol, sorbitol, and sucrose. The most preferred is sucrose.

Fatty Acid Ester of Easily Removable Alcohol

As used herein, the terms "fatty acid ester(s)" and "ester reactant(s)" are intended to include any compound wherein the alcohol portion is easily removed, including polyols and substituted alcohols, etc., but are preferably esters of volatile alcohols, e.g., the $C_1$–$C_4$ alcohols (preferably methyl), 2-methoxy ethyl and benzyl esters of fatty acids containing about eight or more carbon atoms, and mixtures of such esters. Volatile alcohols are highly desirable. Methyl esters are the most highly preferred ester reactants. Suitable ester reactants can be prepared by the reaction of diazoalkanes and fatty acids, or derived by alcoholysis from the fatty acids naturally occurring in fats and oils. Suitable fatty acid esters can be derived from either synthetic or natural, saturated or unsaturated fatty acids and include positional and geometrical isomers. Suitable preferred saturated fatty acids include caprylic, capric, lauric, myristic, palmitic, stearic, arachidic, behenic, isomyristic, isomargaric, myristic, caprylic, and anteisoarachadic. Suitable preferred unsaturated fatty acids include myristoleic, palmitoleic, ricinoleic, linoleic, oleic, elaidic, linolenic, eleasteric, arachidonic, erucic, and erythrogenic acids. Mixtures of fatty acids derived from soybean oil, palm oil, safflower oil, rapeseed oil, canola (low erucic acid), and corn oil are especially preferred for use herein. The fatty acids can be used "as is," and/or after hydrogenation, and/for isomerization, and/for purification. For example, rapeseed provides a good source for $C_{22}$ fatty acid; $C_{16}$–$C_{18_8}$ fatty acid can be provided by tallow, soybean oil, or cottonseed oil; and shorter chain fatty acids can be provided by coconut, palm kernel, or babassu oils. Lard, olive oil, peanut oil, sesame seed oil, and sunflower seed oil, are other natural sources of fatty acids.

Some useful solid polyol fatty acid polyesters are those wherein the ester groups comprise a combination of: (i) long chain, unsaturated fatty acid radicals and/or short chain saturated fatty acid radicals, and (ii) long chain saturated fatty acid radicals, the ratio of (i):(ii) being from about 1:15 to about 2:1, and wherein at least about 15% (preferably at least about 30%, more preferably at least about 50%, and most preferably at least about 60%) by weight of the total fatty acid radicals in the solid polyol polyester are $C_{20}$ or higher saturated fatty acid radicals. The long chain unsaturated fatty acid radicals are typically, but not necessarily, straight chain (i.e., normal) and contain at least about 12 (preferably about 12 to about 26, more preferably about 18 to 22) carbon atoms. The most preferred unsaturated radicals are the $C_{18}$ mono and/or diunsaturated fatty acid radicals. The short chain saturated fatty acid radicals are typically, but not necessarily, normal and contain 2 to 12 (preferably 6 to 12 and most preferably 8 to 12) carbon atoms. More preferred long chain saturated fatty acid radicals are typically, but not necessarily, normal and contain at least 20 (preferably 20 to 26, most preferably 22) carbon atoms. The molar ratio of Group (i) fatty acid radicals to Group (ii) fatty acid radicals in the polyester molecule is from about 1:15 to about 2:1 (preferably from about 1:7 to about 5:3, more preferably from about 1:7 to about 3:5). A typical suitable range is about 3:5 to 4:4. The average degree of esterification of these solid polyol fatty acid polyesters is such that at least 4 of the hydroxyl groups of the polyol are esterified. In the case of sucrose polyesters, from about 7 to 8 of the hydroxyl groups of the polyol are preferably esterified. Typically, substantially all (e.g., at least 85%, preferably at least 95%) of the hydroxyl groups of the polyol are esterified.

Some especially useful solid polyol polyesters prepared by the processes herein contain a combination of: (i) long chain (at least 12 carbon atoms) unsaturated fatty acid radicals, or a mixture of said radicals and saturated short chain ($C_2$–$C_{12}$) fatty acid radicals, and (ii) long chain (at least 20 carbon atoms) saturated fatty acid radicals, in a molar ratio of (i) to (ii) of from about 1:15 to about 2:1, and wherein at least four of the hydroxyl groups of the polyol are esterified.

Examples of long chain unsaturated and polyunsaturated fatty acid radicals for the solid polyol polyesters herein are lauroleate, myristoleate, palmitoleate, oleate, elaidate, erucate, linoleate, linolenate, arachidonate, eicosapentaenoate, and docosahexaenoate. For oxidative stability, the mono- and diunsaturated fatty acid radicals are preferred.

Examples of suitable short chain saturated fatty acid radicals are acetate, butyrate, (caproate), hexanoate (caprylate), decanoate (caprate) and dodecanoate (laurate). Use of more volatile ester reactants may require modification of the process, e.g., use of reflux in the reactors or other means to prevent excessive loss of said reactants.

Examples of suitable long chain saturated fatty acid radicals are eicosanoate (arachidate), docosanoate (behenate), tetracosanoate (lignocerate), and hexacosanoate (cerotate).

Of course, the long chain unsaturated fatty acid radicals can be used singly or in mixtures with each other or in mixtures with the short chain saturated fatty acid radicals, in all proportions. Likewise, the long chain saturated acid radicals can be used in combination with each other in all proportions. Mixed fatty acid radicals from source oils which contain substantial amounts of the desired unsaturated or saturated acids can be used as the fatty acid radicals to prepare compounds of the invention. The mixed fatty acids from the oils should contain at least about 30% (preferably at least about 50%, and most preferably at least about 80%)

of the desired unsaturated or saturated acids. For example, rapeseed oil fatty acids or soybean oil fatty acids can be used instead of pure $C_{12}$–$C_{26}$ unsaturated fatty acids. Hardened (i.e., hydrogenated) high erucic rapeseed oil fatty acids can be used instead of pure $C_{20\text{-}26}$ saturated acids. Preferably the $C_{20}$ and higher acids (or their derivatives, e.g., methyl esters) are concentrated, for example by distillation. The fatty acids from palm kernel oil or coconut oil can be used as a source of $C_8$ to $C_{12}$ acids.

The preferred long chain saturated fatty acid radical is behenate. Preferred solid polyol polyesters of the invention are polyesters of sucrose in which at least 7 of the 8 hydroxyl groups are esterified.

Examples of such solid polyol polyesters are sorbitol hexaester in which the acid ester radicals are palmitoleate and arachidate in a 1:2 molar ratio: the octaester of raffinose in which the acid ester radicals are linoleate and behenate in a 1:3 molar ratio; the heptaester of maltose wherein the esterifying acid radicals are sunflower seed oil fatty acids and lignocerate in a 3:4 molar ratio; the octaester of sucrose wherein the esterifying acid radicals are oleate and behenate in a 2:6 molar ratio; and the octaester of sucrose wherein the esterifying acid radicals are laurate, linoleate and behenate in a 1:3:4 molar ratio. A preferred material is sucrose polyester in which the degree of esterification is 7–8, and in which the fatty acid radicals are $C_{18}$ mono- and/or diunsaturated and behenic, in a molar ratio of unsaturates:behenic of from about 1:7 to about 3:5.

Solid polyol polyesters preferably have complete melting points above about 25° C. (−3.9° F.), more preferably above about 37° C. (2.9° F.), even more preferably above about 50° C. (10° F.) and most preferably above about 60° C. (15.5° F.). Melting points reported herein are measured by Differential Scanning Calorimetry (DSC). These solid materials have the ability to trap relatively large amounts of oil within their crystal structure. As a consequence, they can be used as "hardstocks" by blending them in amounts of from about 1% to about 50% (typically from about 1% to about 25%) with liquid oils, to prepare semi-solid compositions. A typical suitable range is from about 10% to about 25%. The oils for these compositions can be conventional digestible triglyceride oils such as cottonseed, corn, canola, or soybean oil, or nondigestible edible oils.

As disclosed herein before, other suitable polyol polyesters that can be prepared by the processes herein include the polyol polyesters disclosed in the patents incorporated herein by reference, especially U.S. Pat. Nos.: 3,963,699; 4,517,360; and 4,518,772.

The fatty acid composition (FAC) of the polyol polyesters can be determined by gas chromatography, using a Hewlett-Packard Model 5712A gas chromatograph equipped with a thermal conductivity detector and a Hewlett-Packard Mode 17671A automatic sampler. The chromatographic method used is described in *Official Methods and Recommended Practices of the American Oil Chemists Society.* 3rd Ed., 1984, Procedures 1-$C_e$62 (incorporated herein by reference).

It is very important for the preparation of improved polyol polyesters that the fatty acid esters be highly purified to remove color/odor materials, oxidation products, and/or their precursors. Such materials include those that have a color, odor, or taste that is objectionable, or which develop an objectionable color, odor, or taste upon heat treatment and/for oxidation. In addition, highly polar materials which coat the catalyst surface should be removed. Preferably, the carbonyl value should be less than about 200 ppm, more preferably less than about 100 ppm, and even more preferably less than about 50 ppm. Processes for preparing such fatty acid esters are disclosed in U.S. Pat. No. 4,931,552, Gibson et al., issued Jun. 5, 1990, said patent being incorporated herein by reference. The percent transmittance at 375 nm with a heptane standard should be greater than zero, preferably greater than about 60, most preferably greater than about 80. For typical ester sources without added colored materials, these values define operable reactants. I.e., the carbonyl content is generally indicative of the total level of polar materials present. The low level of color/odor materials and/or oxidation products in the reactants helps provide improved color polyol polyester products that can be further improved by a combination of the process improvements set forth herein.

Removal of Unreacted Polyol and/or Large Particle Catalyst at an Early Stage of the Reaction Unreacted polyol and/or large particle catalyst are desirably removed at an early stage of the reaction, e.g., before the polyol is esterified to more than about 75% and, preferably, (a) after the degree of interesterification is greater than about 15%, preferably greater than about 40%, and (b) while any soap that is present is still soluble in the reaction mixture. This removal results in surprisingly fast reaction kinetics and more rapid and high conversion to highly esterified product having good color without the need to add additional catalyst thereafter. Removal at an early stage is more convenient than in a later stage due to the low viscosity of the reaction mixture and minimizes production of unwanted by-products. Unreacted polyol, such as sucrose, can interfere with the orderly progress of the reaction in the later stages where it limits the desired interesterification reaction by degrading, and/or preferentially reacting with the active form of the catalyst and/or by continuing to create undesirable by-products such as color bodies.

In a preferred embodiment the soap and polyol can be co-milled in a suitable mill such as a jit mill, hammer mill or air swept mill.

Removal of unreacted polyol and/or large size catalyst can be accomplished by, e.g., filtration and/or by centrifigation if the polyol is a solid in the reaction mixture. The resulting reaction mixture that is free of unreacted polyol will then react faster and reach the desired degree of esterification quicker than if the polyol remains. The key to the improved reaction kinetics is to lower the level of unreacted polyol to less than about 0.5%, and preferably less than about 0.20% and most preferably the reaction is substantially free of any unreacted polyol, i.e., less than 0.02%. The filtered polyol and/or any catalyst removed with it can be returned to an earlier stage of the reaction or discarded.

One way to keep the unreacted polyol level below about 0.5% is to control the reaction conditions in the first stage so that less than 0.5% polyol remains, and more preferably below about 0.29%.

The removal of sucrose or polyol at the beginning of the second stage facilitates the use of lower second stage reaction temperatures while getting surprisingly fast conversion to octaester of sucrose.

Catalyst

The basic catalysts generally suitable for use in preparing the polyol polyesters are those selected from the group consisting of alkali metals, such as sodium, lithium and potassium: alloys of two or more alkali metals, such as sodium-lithium and sodium-potassium alloys; alkali metal hydrides, such as sodium, lithium and potassium hydride; and alkali metal alkoxides, such as potassium t-butoxide, potassium methoxide, and/or sodium methoxide. Potassium methoxide is preferred, especially when used with potassium soap.

In another particularly preferred embodiment of the present invention, the basic catalyst used in the reaction is potassium carbonate, sodium carbonate, barium carbonate, or mixtures of these compounds having particle sizes that are less than about 100 microns, preferably less than about 50 microns. It has been found that when these specific compounds are used as catalysts, increased yields of light colored higher polyol polyesters are obtained when compared to essentially identical reactions carried out using more conventional catalysts, such as sodium hydride, potassium hydride, soap, or sodium methoxide. These preferred catalysts can also be used in admixture with the more conventional basic catalysts, described above. Potassium carbonate and/or potassium methoxide are the most preferred catalysts for use herein. The use of these catalysts is further disclosed and claimed in U.S. Pat. No. 4,517,360, Volpenhein, issued May 14, 1985, said patent being incorporated herein by reference.

More reactive catalysts such as potassium or sodium methoxide should be protected until their addition into the reaction mixture. Preferably the catalyst should be suspended in or more preferably encapsulated by a material that will either be present in the reaction mixture or be readily separated from the reaction mixture. Suitable encapsulating agents include said alkyl esters of, e.g., $C_{16}$–$C_{22}$ fatty acids. Addition of these more alkaline, reactive catalysts in the later stages after the polyol has an average degree of esterification of more than about 60%, preferably more than about 85%, provides improved reaction kinetics and results in a greater degree of esterification of the polyol yet does not create the level of color/odor materials that would be created if such catalysts were present from the start of the reaction.

The level of catalyst is kept as low as possible, as discussed more fully hereinafter, typically from about 0.01 to about 0.5, preferably from about 0.01 to about 0.1, more preferably from about 0.02 to about 0.05, moles of catalyst per mole of polyol. The level of catalyst can be lowered to the least amount that is effective to give a reasonable rate of reaction. It is possible to have very fast reactions using only the residual base in, e.g., the soap emulsifier commonly used in such reactions. It is desirable to keep the level of base as low as possible to minimize formation of color and/or odor bodies and/or excess soap and/or by-products. It is also desirable to effect the removal of oversize catalyst after the first phase of the reaction, and/or the destruction and removal of the catalyst after the reaction has reached the desired end point.

Small Particle Size Polyol Obtained by Mechanical Size Reduction

The use of small particle size polyol, e.g., sucrose, in esterification reactions to form polyol polyesters is highly desirable to improve the speed of reaction. In reactions that use a solvent to form a homogeneous reaction mixture, there is little need for the small particle size, since the polyol is dissolved by the solvent. However, in solventless, heterogeneous reactions of the type herein, small particle size is highly desirable because smaller particles have a larger surface that are exposed to the liquid which greatly improves the reaction kinetics. The small particle size can also be achieved by art-disclosed methods in which the polyol, e.g., sucrose, is dissolved in water and then the water is removed after the other reactant ingredients and/or catalyst are present to form small particles of the polyol in situ. There is no general consensus, or appreciation, in such art that the primary factor that improves the reaction is the resulting small particle size of the polyol. Furthermore, although this preliminary step of dissolving the polyol in water provides the desired small particle size, it requires the removal of water from the reaction mixture, usually at a time when other ingredients are present, and the presence of water can promote the formation of undesirable side products. It is especially undesirable in a continuous process.

An improved reaction can be achieved without the use of solvent, either in a preliminary step, or in the reaction itself, if the particle size of the solid polyol is less than about 100 microns, preferably less than about 50 microns, more preferably less than about 10 microns. These particle sizes can be achieved, e.g., by a combination of grinding, milling, and/or sieving. It is surprising that the particles of these sizes, prepared by simple mechanical size reduction methods, provide the benefits of the prior art processes requiring water solutions of that give particle diameters below one micron.

Low Catalyst Level and Preferred Small Particle Size Catalyst in a Continuous Process In a continuous process, a low level of catalyst is highly desirable. A low level of catalyst, below about one half of a mole per mole of polyol, still provides fast reactions with little formation of undesirable materials. This is because when the levels of free fatty acids are low, there is much less surface poisoning of the catalyst. The surprising speed of the reaction with a low level of catalyst permits the low level of catalyst to be used in a continuous process where a long reaction time would be costly. The preferred level of catalyst is from about 0.01 to about 0.1, preferably from about 0.02 to about 0.05, mole per mole of polyol. With these levels of catalyst, the reaction proceeds at a fast rate and the amount of catalyst and/or soap, that must be removed at the end of the reaction is much less. The small amount of base that typically accompanies soap used as an emulsifier can promote the reaction. It is often desirable to add a more active catalyst like an alkali metal alcoholate, especially $C_{1-4}$ and desirably sodium and/or potassium alcoholates such as potassium and/or sodium methoxide, to the reaction mixture at a later stage of the reaction to further increase the speed of the reaction.

Homogeneous catalysts are desirable for the reaction, solid catalysts can be used.

The preferred particle size of any solid catalyst is less than about 100 microns, preferably less than about 50 microns, and even more preferably less than about 10 microns. When low levels of catalyst are used, it is important to use smaller particle sizes of catalysts and/or sucrose.

Emulsifier

Emulsifiers help to solubilize the polyol in the methyl fatty acid esters. Polyol fatty acid esters having less than 4 hydroxy groups esterified with fatty acids are useful emulsifiers. Highly preferred emulsifiers are sucrose mono esters, diesters and triesters of $C_{12}$–$C_{20}$ fatty acids. It is preferred that the lower polyol fatty acid esters be the same as the polyol polyester being synthesized to avoid separation problems as the completion of the reaction.

These lower polyol esters are preferred emulsifiers. One way to obtain them is by generation in the reaction itself. This is accomplished by reacting the polyol with fatty acids under conditions that encourages formation of lower esters initially and then adding more fatty acids later. Alkali metal soaps can also be used as emulsifiers in the processes described herein. As used herein, the term "alkali metal fatty acid soap" is intended to include the alkali metal salts of saturated and unsaturated fatty acids having from about 8 to about 18 carbon atoms. Suitable alkali metal fatty acid soaps include, for example, lithium, sodium, potassium, rubidium, and cesium salts of the fatty acids described above. Mixtures of fatty acids derived from soybean oil, sunflower oil, safflower oil, and corn oil are preferred for use herein. Preferred alkali metal fatty acid soaps include potassium soap made from soybean oil, preferably hydrogenated soybean oil.

The level of soap should be at least enough to dissolve the polyol at an acceptable rate. The level of soap can be reduced as a result of using smaller particle polyol, e.g., sucrose, and/or reaction conditions that favor the solubilization of the polyol. Excessive soap can cause foaming and undesirable thickening. The level of soap in the first stage of the reaction is usually from about 0.001 to about 0.6, preferably from about 0.05 to about 0.1 moles of soap per mole of polyol. The soap is preferably used in combination with another emulsifier, preferably with the lower esters of the polyol and the fatty acid which are present either by being added as part of the initial reaction mixture, or by backmixing. The desire is to have little or no soap in the second stage as it increases the viscosity of the reaction and inhibits alcohol transfer from the reaction mixture. This will increase the rate of the reaction.

After the average degree of esterification reaches about 60%, the soap is no longer needed to facilitate the reaction and, therefore, can be removed. Soap emulsifier is not essential after the polyol has reacted once and there is sufficient lower ester to maintain the homogeniety of the reaction mixture.

Removal of soap can be accomplished, e.g., by filtration, centrifugation, etc., since the soap is relatively insoluble in the reaction mixture at such higher degrees of esterification. The resulting filtered reaction mixture does not need to be recatalyzed, and, the reaction proceeds at a much higher rate than if the soap were present. The filtered reaction mixture typically has a soap level of less than about 0.5, preferably less than about 0.1 moles of soap per mole of polyol, more preferably less than about 0.05 moles of soap per mole of polyol. The filtered material can be returned to the initial stage of the reaction. However, since the composition of the filtered material can vary, it is usually better not to recycle it.

Back Mixing

It is highly desirable to conduct the initial stage, or stages, of the reaction under back-mixing conditions to maintain the degree of esterification between about 10% (preferably 20%) and about 50%, preferably between about 35% and about 45%. This degree of esterification provides sufficient lower partial polyol polyester to aid in the solubilization of the poorly soluble polyol and to provide a stable heterogeneous reaction mixture that minimizes unreacted polyol, and the distribution/composition and/or level of lower esters and/or soap that cause foaming is low enough to permit continuous reaction without overfoaming. Levels of conversion below about 20% can require low levels of soap, higher pressure or vigorous agitation to avoid overfoaming. In a continuous reaction, the individual reactants can be added to the first stage at a rate that maintains the desired degree of esterification and yet provides sufficient yield from the first stage to maintain the reaction in the subsequent stage, or stages.

It is desirable in the initial stage, or stages, of the process, and especially of a continuous process, to have a relatively high degree of completion. While the preferred degree of esterification is at least about 35%, more preferably at least about 45%, to minimize the amount of esterification that must take place in the final stages, removal of essentially all of the unreacted sucrose before entering the final stages greatly facilitates the reaction. Preferably, the final stages are preferably carried out under conditions of plug flow. In the final stages, the reaction conditions are more stringent (lower pressure or higher sparge rates, or longer residence time etc.) and therefore more costly. Decreasing the time of the later stages and/or the size of the reactor is therefore desirable. Maintenance of the appropriate composition for solubilizing the polyol in the first stage is assisted by withholding a portion of the ester reactant from this initial stage, as described in U.S. Pat No. 3,963,699, supra, incorporated herein by reference. In the initial stage, it is preferable to use only about 10% to about 50% of the total ester reactant, with the remainder being added in the later stages, especially where there are plug flow conditions.

Backmixing can be achieved in a continuous reaction, for example, by continually recycling a portion of the first stage reaction stream and/or by carrying out the reaction in a well agitated vessel (or, e.g., two vessels in series, or any other similar configuration that has hydrodynamically similar mixing conditions) where the reactants are continually added and the product is removed at rates that maintain the desired level of esterification. Although it is possible to start with plug flow conditions, the initial solubility of sucrose is low at the start of the reaction; the risk of unacceptable levels of foam when the degree of esterification is less than about 20% is great; and the resulting instability of the reaction mixture gives variable, poorly controlled esterification of the polyol. Without filtration of the unreacted reactants as discussed herein before, the conversion of the polyol can be poor and therefore plug flow is undesirable in the initial stages, especially without recycling.

If residual sucrose is detected in the first stage product, the product of the first stage is preferably filtered, or otherwise treated to remove substantially all of the unreacted polyol less than 0.5% should remain, and the unreacted solids are returned to the first stage, or, preferably, if at a lower level, discarded, since the ingredients are present, at least initially, at varying and unknown levels. If the reaction contains only low levels of soap emulsifier and catalyst, as preferred herein, the amount of material to be separated is minimal. Once steady state is achieved in a continuous reaction, the separated material can be cleaned up, e.g., by a purge stream, and recycled.

Backmixing in a batch process, can be approximated by using part of a previous batch that has the right degree of esterification, and adding reactants to the batch while the reaction is continuing until the appropriate degree of completion is reached, whereupon the addition of reactants is stopped and the reaction is taken to completion. A "semi-batch" reaction can be run by continually bringing batches to the appropriate intermediate degree of completion and then transferring at least the major portion of the batch to another vessel where the reaction is taken to completion.

Apparatus that is suitable for backmixing, and/or plug flow conditions, as discussed hereinafter, is disclosed in U.S. Pat. No. : 3,567,396, Setzler, issued Mar. 2, 1971; U.S. Pat. No. 3,679,368, Balint, et al., issued Jul. 25, 1972; U.S. Pat. No. 4,449,828, Mansour, issued May 22, 1984; U.S. Pat. No. 4,472,061, Mansour, issued Sep. 18, 1984; U.S. Pat. No. 4,543,194, Spence et al., issued Sep. 24, 1985; and 4,615, 870, Armstrong et al., issued Oct. 7, 1986, all of said patents being incorporated herein by reference. Other disclosures of suitable processes and apparatus can be found in: The Degree of Mixing in Continuous Flow Systems, Zwietering, Chemical Engineering Science, pp. 1–15, Vol. 11, No. 1 (1959); Continuous Flow Stirred-Tank Reactor Systems, MacDonald and Piret, Chemical Engineering Progress, Vol. 47, No. 7, pp. 363–8 (July 1951); and Reaction Kinetics in a Tubular Reactor, Baron, Manning and Johnstone, Chemical Engineering Progress, Vol. 48, No. 3, pp. 125–132 (March 1952), all of said articles being incorporated herein by reference.

Use of Plug-Flow and/or Batch Conditions in the Final Stages to Achieve High Degree of Complete Esterification The final stage, or stages, of the reaction should be carried out under plug-flow, or batch, conditions to prevent back-mixing and thereby achieve high degrees of esterification. This plug flow can be approximated by feeding the output of the initial stage into a series of at least two continuous stirred tank reactors, but preferably is accomplished more efficiently in a continuous reactor, for example, in a tubular reactor and/or packed column and/or tray reactor and/or falling or rising film reactor, using more nearly plug-flow reactor apparatus. As discussed above, the plug flow conditions should be used after the degree of esterification of said polyol has reached at least about 35 to about 45%. The final degree of esterification should be at least about 70%, preferably at least about 97%.

The total ester reactant to polyol esterifiable site in the final stages should be from about 0.9:1 to about 1.4:1, preferably from about 1:1 to about 1.2:1. The reduction or removal of soap is preferred for column or film reactors to reduce the viscosity for improved operation.

In either a batch, semi-batch, or continuous process, the combination of (1) small particle size polyol, preferably obtained by mechanical size reduction to avoid the complications associated with solvent removal, (2) low levels of catalyst, preferably having a small particle size, and (3) low levels of soap is highly desirable since such a combination provides a fast reaction while minimizing the amount of unwanted materials that are present and that must eventually be removed.

The combination of polyol removal with these improvements is desirable to improve both the speed of esterification and the degree of esterification completeness. Polyol that has not been dissolved in the early stage(s) of the reaction can interfere with the degree of completion.

Higher pressures have the additional advantage of reducing air leakage into the reaction system. In a heated reaction system, air will react immediately with any fatty material. This will degrade the color, odor, flavor and physical properties of the fully esterified product Reaction of air with fatty materials will also produce short chain and unsaturated soap, which will cause the reaction mixture to thicken appreciably in the second stage. This thickening will slow down the reaction by limiting the mass transfer of methanol or alcohol by-product out of the liquid phase. Thus, air leakage will detrimentally affect both the reaction rate and product quality.

Higher pressure, especially in the last stages of the reaction and more especially in the last stages of a continuous process is desirable since the combination makes it possible to fabricate the reaction apparatus without making provision for the maintenance of the more extreme conditions required by prior processes and allows for savings in energy usage in addition to the avoidance of the formation of undesirable and/or unneeded by-products. The savings are even greater in the preferred "plug-flow" final stages of the process where the conditions have to be maintained throughout the portion of the apparatus where the final stages of the reaction occur.

The combination of backmixing in the initial stage(s) and plug-flow conditions in the later stage(s) is highly preferred, especially for a continuous process, or mixed batch/continuous process, or continuous/batch process as it helps maintain optimum conditions for initiating the reaction between ingredients that are normally not compatible and then maximizing the final degree of esterification of the polyol.

The preferred products of the processes described herein have a detectable difatty alkyl ketone content that is less than about 300 ppm, preferably less than about 200 ppm, more preferably less than about 100 ppm. The preferred products contain less than about 4,000 ppm. preferably less than about 3,000 ppm of materials other than the desired polyol polyester. However, in products made by commercial processes of the types disclosed herein there is usually a detectable level, typically more than about 50 ppm of such other materials. The very low levels of by-products are achieved by the improvements herein, using good quality methyl esters as described herein before, and applying finished product clean-up procedures as described hereinafter.

The Reaction

In general, by way of example, an initial heterogeneous reaction mixture comprises from about 10% to about 30%, preferably from about 14% to about 18%, by weight of polyol; from about 0.3 to about 1.4, preferably from about 0.3 to about 0.7 moles of fatty acid ester per esterifiable hydroxy groups on the polyol; an effective amount of lower partial polyol esters or from about 0.001 to about 0.6, preferably from about 0.05 to about 0.1, moles of alkali metal fatty acid soap per mole of the polyol; and from about 0.01 to about 0.1 preferably from about 0.02 to about 0.05, mole per mole of the polyol of basic catalyst component. If desired, the reaction can be run in one or more reactors, although two reactors is preferable. In any later stage, additional fatty acid esters and, possibly, a more reactive catalyst can be added. After the initial stage, and before entering stage 2 any unreacted polyol is removed or decreased to a level of less than about 0.5% more preferably less than about 0.2%. In any second, or later step, additional fatty acid ester can be added to raise the overall ratio of fatty acyl groups to the esterifiable hydroxy sites on the polyol to from about 0.9:1 to about 1.4:1, preferably from about 1:1 to about 1.2:1. A preferred catalyst in the initial step is potassium carbonate, potassium methoxide, and/for residual base in the soap, as described herein before and, in any later step, the preferred catalysts are potassium and/or sodium carbonates and/or methoxides.

The reaction mixture is heated to a temperature within the range from about 130° C. to about 150° C., under vacuum with or without inert gas sparging or at or about atmospheric pressure with inert gas sparging. It is highly preferred that the reaction mixture, or mixtures, be stirred as vigorously as possible. The mixing is increased in the subsequent stages by the preferred step of sparging with an inert gas, preferably nitrogen, carbon dioxide, low molecular weight hydrocarbons. With sparging, the removal of volatile alcohol produced in the reaction is promoted and the reaction rate is increased.

Finished Product Clean-up

After the reaction has reached the desired state of completion, the catalyst, the excess fatty esters, and the emulsifier, e.g., soap, must be removed if they cannot be used in the eventual consumption of the polyol fatty acid polyesters. The soap and catalyst can be removed to a large extent by a water separation step. However, it is an advantage of the processes herein that the level of catalyst, soap, and/or unreacted polyol and/or ester reactant present can be reduced drastically. Water is added, preferably at a ratio of from about 0.5:1 to about 10:1 relative to the amount of soap being removed. This low water level which is much less than would normally be considered desirable, surprisingly results in a better removal of the soap and catalyst than is achieved with more water, e.g., 20–40%. Separation of the soap and catalyst is facilitated by passing the water and reaction mixture through a centrifuge.

After centrifugation, the reaction mix can still contain an undesirable level of residual soap and/or color bodies. It is useful to repeat the water washing step followed by gravity or centrifugal separation of the aqueous phase. A subsequent vacuum drying and adsorptive bleaching operation can be used in combination with, or instead of, this second washing step. Drying and/or adsorptive bleaching operations, that use adsorbents such as bleaching earth and/or silica gel, are typical operations for processing edible oils. The adsorbents are added, preferably at a level of from about 0.1% to about 10% by weight of the dry reaction mix. After the bleaching operation is completed, the adsorbents are removed from the reaction mixture by filtration. The second stage water washing, and/or drying, and/or adsorptive bleaching completes the removal of soap and color bodies and prepares the reaction mixture for removal of any unreacted fatty acid ester.

A useful known process that can be used, in addition to the improvements described hereinafter, for removing unreacted materials, e.g., fatty acid ester reactant, and any other undesirable materials comprises a high temperature vacuum steam distillation process, and involves deaerating the polyol polyester to a level of less than about 0.10% by volume of dissolved oxygen and heating the deaerated oil to a temperature between about 390° F. (200° C.) and about 480° F. (250° C.) and then stripping with a stripping medium in the amount of about 0.2% to about 20% by weight of the oil at an absolute pressure of less than about 15 mm Hg for a time of between about 5 seconds and about 15 minutes. This vacuum stripping at very high temperatures for short residence times minimizes the content of undesirable materials. It is desirable to either maintain the temperature below about 450° F. (230° C.), preferably less than about 350° F. (about 180° C.), in a batch deodorizer, or admix the polyol polyester with a fatty acid triglyceride to protect the polyol polyester from excessive thermal degradation. Removal of such unreacted materials and other undesirable materials can also be desirably effected in a wiped film heat exchanger or other film evaporator.

Another useful improvement in finished product clean-up, involves adding a small amount of solubilised base (e.g., potassium hydroxide or potassium methoxide, solubilised in methanol) before distillation of any excess fatty acid ester reactant. The solubilised base improves the oxidative stability of the polyol fatty acid polyesters. The solvent for the base is preferably non-aqueous and the pH, measured at 120° F. (48.9° C.) on a 10% polyol fatty acid polyester solution in water/isopropanol, is from about 6.5 to about 9.

After the initial treatments, as described herein before, the undesirable materials can reform due to degradation of the oil/fatty acid ester. In addition, some undesirable color materials remain after the high temperature vacuum steam distillation process. The very low levels of color/odor/flavor materials, precursors, and/or oxidation products most preferred for use herein can be achieved by a clean-up procedure comprising one or more steps including, but not limited to:

(1) a step involving treatment with silica gel having the following properties: (a) a particle size of ranging from about 10 to about 30, preferably from about 20 to about 25 microns; (b) average pore diameter of from about 50 to about 70 microns; (c) surface area of from about 720 to about 800, preferably from about 770 to about 800 $m^2/gm$; (d) pore volume of from about 0.9 to about 1.9, preferably from about 1.2 to about 1.4 $cm^3/gm$; (e) a pH of from about 5 to about 8, preferably from about 5 to about 7.3 measured at a level of about 5% in water; and (f) total volatiles of less than about 20%, preferably from about 6.5% to about 10.5%, and more preferably from about 8% to about 10.5%. Such silica gels are extremely effective as compared to other known materials. Said silica gel is added to the product at levels of from about 0.25% to about 5%, preferably from about 1% to about 2%.

The use of the silica gel inevitably introduces oxygen, from entrapped air, into the polyester. It has been discovered, surprisingly, that oxygen can provide a benefit. Therefore, another process step involves introducing oxygen up to about saturation level, as a separate step and/for by the silica gel, and then raising the temperature to at least about 200° F. (about 90° C.), preferably at least about 380° F. (about 190° C.), but less than about 425° F. (about 220° C.), preferably less than about 400° F. (about 205° C.), to produce peroxygen groups and hold the product at the elevated temperature for a period of time sufficient to reduce the peroxygen content and/or reduce the content of colored materials present, e.g., from about 1 to about 150 minutes, preferably from about 1 to about 20 minutes, and most preferably from about 5 to about 10 minutes. (The level of oxygen in the polyol polyester is believed to be from about 0.001 to about 0.16 volumes of oxygen per volume of polyol polyester assuming similar values to those reported for triglycerides.) This can be accomplished separately, or in combination with a steam deodorization step, as described herein before. The time should not be so long as to start again increasing the color. When this oxygen/heat treatment step is used, it is possible to use a wider range of silica gels in place of the preferred silica gel of step (1) and achieve acceptable results. The best results, however, are achieved with the preferred silica gel.

Any steam deodorization steps prior to the silica gel bleaching step and/or after the heat treatment step can be accomplished in the presence of a conventional triglyceride in ratios of higher polyol polyester to triglyceride of from about 1:10 to about 10:1, preferably from about 1:5 to about 5:1, more preferably from about 1:3 to about 3:1. This "codeodorization" minimizes thermal degradation of said polyester. The operating conditions for codeodorization are from about 300° F. (about 150° C.) to about 600° F. (about 315° C.), preferably from about 350–525° F. (about 175–275° C.); about 0.1–20 mm Hg (preferably about 1–10 mm Hg) vacuum; and steam to product ratio of about 0.001–0.30 (preferably 0.005–0.10). As compared to deodorization of the polyol polyester by itself. codeodorization permits the use of higher temperatures, e.g., from about 300OF (150° C.) to about 600° F. (315° C.), preferably from about 350° F. (175° C.) to about 525° F. (275° C.), and/or longer times without excessive degradation and can be desirable if equipment limitations are present The triglyceride is usefully any common triglyceride, e.g., those derived from cottonseed, peanut, safflower, sunflower, coconut, rapeseed, canola, palm, palm kernel, and or soybean oils.

When the initial reactants have been properly cleaned up and the preceding clean-up steps have been applied properly, the color of the polyol polyester is less than about 3.0, preferably less than about 1.2, more preferably less than about 0.8 Lovibond Red, and the flavor grade of the polyol polyester is at least 7, preferably at least 8 panel score units (psu) as measured by a panel of experts using a grade system in which 10 is bland and 1 is severely oxidized. Such a finished polyol polyester has improved oxidative, flavor, and thermal stability during its subsequent uses. When combined with a typical triglyceride, containing natural antioxidants, in ratios of polyol polyester to triglyceride of from about 1:10 to about 10:1, preferably at ratios of from about 1:3 to about 3:1, more preferably at ratios of from about 1:3 to about 1:1, the stability is further surprisingly enhanced. Apparently, the reactive materials are reduced to a level where the natural antioxidants can provide improved long term stability.

Combinations of one or more of these cleanup steps reduce the quantity of undesired materials to a very low level, typically from about 50 ppm to about 4,000 ppm, most preferably less than about 3,000 ppm. For example, the products of the processes described herein can contain less than about 300 ppm, preferably less than about 200 ppm, more preferably less than about 100 ppm of di-fattyalkylketone which is typically present in products prepared by (fatty acid ester)/polyol interesterification reactions. This is especially true when the methyl ester excess is low and/or lower temperatures are used.

Especially preferred polyol polyesters are those which have been esterified to a level of more than about 50%, preferably more than about 70%, and more preferably more than about 80% octaester for use in preparing liquid shortenings and from about 80% to about 90% octaester for "solid" shortenings. Such sucrose polyesters have superior thermal stability, especially when they contain only low levels of color/odor materials and/or other oxidation products.

All percentages, parts and ratios herein are by weight unless otherwise specified.

EXAMPLE 1

This example describes the first stage of the reaction, i.e., reacting each polyol molecule with at least one fatty acid methyl ester molecule. The reactors in this example are two stainless steel tank reactors in series, each about 4.5 feet in diameter, and each having an agitator, a liquid level control system, a heater, a recirculation pump, and temperature and pressure sensors. The agitators are run at about 200 RPM. Sucrose, cottonseed fatty acid methyl esters, potassium stearate, and potassium carbonate are fed into the first reactor in the series at approximately the following molar ratios:

| Materials | Molar Ratio |
| --- | --- |
| Fatty acid methyl ester:sucrose | 5:1 |
| Potassium stearate:sucrose | 0.2:1 |
| Potassium carbonate:sucrose | 0.1:1 |

Both reactors are operated at about 275° F. (135° C.), and vacuum is applied to both reactors to maintain pressure at about 15 mm Hg. Both reactors act as continuous stirred tank, reactors (CSTR's), i.e., the reactors are designed to have backmixing. Backmixing is desirable in this stage of the reaction so that sucrose mono-, di-, and triesters that are the product of the reaction are maintained in intimate contact with incoming unreacted polyol. The sucrose mono-, di-, and triesters solubilize the solid sucrose into the reaction mixture, enabling it to react more readily with the fatty acid lower alkyl esters. The average residence time of the reaction mixture in the first reactor is about 1 hour. The reaction mixture is then pumped from the first reactor to the second reactor at the same rate as the in-going feed material so that the level in the first reactor is kept constant. The reaction material pumped into the second reactor has an average residence time of about 1.5 hours in that reactor. Reaction material is pumped out of the second reactor at the same rate as the in-going feed to keep the level in the second reactor constant The reaction material from the second reactor is then transferred to the column reactor. The sucrose at this point is about 50% esterified, with an unreacted sucrose level of about 0.5%.

EXAMPLE 2

Reaction material from the first stage of the reaction (Example 1) is pumped continuously into a column reactor along with additional fatty acid methyl esters to bring the total fatty acid methyl ester:sucrose molar ratio to about 11:1. Potassium methoxide solution is continuously added to the top of the column at a weight ratio of I gram of potassium methoxide solution for each 26 lbs. of incoming feed material. The column is designed to approximate plug flow, and to provide intimate contacting between the stripping gas and the reaction liquid. The column consists of a section of glass pipe approximately 12 inches in diameter and 72 inches long. Six plates are placed in the column at equal intervals that segment the column into six sections. Each plat has several small holes that allow the nitrogen gas to pass upward through the plate, and overflow weirs and downcomer tubes that allow the liquid to flow from one segment to another. This design is similar to the tray design common in many distillation column applications. Under normal operating conditions only gas will move (upward) through the small holes, and only liquid will move downward through the overflow weirs and downcomers. The holes for the inert gas are about 3/16-inch in diameter, and the open area on the plate due to these holes is about 5% of the total surface area of the plate.

Each section has a 6-blade turbine type agitator, operated at about 380 RPM. The agitator diameter is approximately one-half the diameter of the column. The reaction material from the Example 2 is fed into the top of the column, along with potassium methoxide solution (25% in methanol) and travels downward through the column through the over flow weirs and downcomer tubes. Nitrogen is introduced at the bottom of the column and travels upward through the column, through the center holes, counter current to the liquid flow. In each segment, the nitrogen is dispersed into the liquid by the agitators, and strips the methanol by-product from the reaction mixture. The nitrogen and methanol proceed upward through the column (propelled by buoyant forces), from section to section. The gas is exhausted from the column when it reaches the top. The reaction product is pumped from the bottom of the column. The reactor is operated at about 275° F. (135° C.), at about atmospheric pressure at the top of the column, and at about 1 psig above atmospheric pressure at the bottom of the column. The weight ratio of nitrogen to the incoming liquid feed is about 1.5:1, and the average residence time of the liquid in the column is about 2 hours. Upon reaching steady state, this reaction gives a product in which the sucrose is approximately 90% esterified, containing about 43% sucrose octaester. Conversion data versus time from the state of continuous feed is shown below.

| Time from the start of continuous feed | % sucrose octaester |
| --- | --- |
| 2 hours | 32 |
| 3 hours | 39 |
| 4 hours | 40 |
| 5 hours | 44 |
| 6 hours | 43 |

EXAMPLE 3

A reaction the same as Example 2 was performed, except that prior to the introduction of the partially esterified sucrose (from Example 1) into the top of the column, the residual unreacted particulate sucrose was removed by settling. Analysis of the material being fed into the top of the column shows less than 0.05% unreacted sucrose (versus 0.5% unreacted sucrose in Example 6). All process conditions in this example are the same as Example 3. Upon reaching steady state, this reaction gives a product in which the sucrose is approximately 99.6% esterified, containing about 97% sucrose octaester. Conversion data versus time from the start of continuous feed is shown below.

| Time from the start of continuous feed | % sucrose octaester |
| --- | --- |
| 2 hours | 80 |
| 3 hours | 96 |
| 4 hours | 96 |
| 5 hours | 97 |
| 6 hours | 97 |

The reaction in this example achieves a much higher degree of conversion to sucrose octaester in the same residence time as Example 3, indicating a much faster reaction. This was due to the reduction of unreacted sucrose in the feed to the column from 0.5% in Example 3 to less than 0.05% in this example.

EXAMPLE 4

This example shows a series of reactions with differing amounts of unreacted sucrose in the starting material. Partially esterified reaction material is prepared similar to the method in Example 1. Three different feed materials are prepared. Each contains sucrose esters that are approximately 50% esterified, but the amounts of unreacted sucrose in each material is approximately 1%, 0.25%, and <0.05% respectively. Each of these feed materials is then fully esterified in 1-liter glass batch reaction systems. Each reaction system has an agitator, heating mantle, temperature control system, inlet for nitrogen stripping gas, and outlet for exhaust gas. Approximately 300 grams of each feed are added to each reactor along with about 0.8 grams of potassium methoxide solution. Each reactor is heated to about 275° F. (135° C.), and the reaction material in each reactor is stripped with about 12 grams per minute of nitrogen in order to remove the methanol by-produce from the reaction. The table below shows the amount of sucrose octaester in each reactor at 1,2 and 3 hours after the start of each reaction.

| Time after start of the reaction | % unreacted sucrose in starting material | | |
| --- | --- | --- | --- |
| | <0.05% | 0.25% | 1% |
| 1 hour | 72 | 50 | 64 |
| 2 hours | 96 | 88 | 69 |
| 3 hours | 98 | 97 | 69 |

This example demonstrates that reducing the amount of unreacted sucrose prior to the second stage of the reaction leads to a faster reaction rate, and a higher degree of conversion to sucrose octaester.

We claim:

1. A continuous, solvent free process for preparing polyol fatty acid polyesters by interesterifying polyol containing more than about four esterifiable hydroxy groups and fatty acid ester wherein
    (1) the initial catalyst level is from about 0.001 to about 0.5 mole of catalyst per mole of polyol;
    (2) the polyol is a particulate solid having a particle size of less than 100 microns and when the degree of esterification of the polyol has reached about 15% but is no more than 75%, substantially all unreacted polyol particles are removed or substantially completely reacted; and
    (3) the initial stages of the reaction are carried out under conditions which maintain a level of lower partial fatty acid esters of said polyol in an emulsifying amount.

2. A process according to claim 1 wherein the reaction is substantially free of unreacted polyol when the degree of esterification is about 40%.

3. A process according to claim 2 wherein the amount of unreacted polyol is less than 0.5%.

4. A process according to claim 2 wherein the amount of unreacted polyol is less than 0.2%.

5. A process according to claim 3 wherein the reaction contains an emulsifier selected from the group consisting of lower polyol esters, soaps and mixtures thereof.

6. A process according to claim 4 wherein the unreacted polyol is removed before any soap present becomes insoluble.

7. A process according to claim 3 wherein the fatty acid ester is an ester of a volatile alcohol and wherein the pressure of the reaction is maintained at from about 5 to about 300 mm Hg and the removal of the volatile alcohol that results for the interesterification reaction is assisted by increasing the mass transfer area of the reaction mixture.

8. A process according to claim 6 wherein the particle size of the polyol is less than about 50 microns.

9. A process according to claim 7 wherein the particle size of the polyol is less than about 10 microns.

10. A process according to claim 8 wherein the initial level of emulsifier in the first stage of the reaction is from about 0.001 to about 0.6 mole per mole of polyol.

11. A process according to claim 9 wherein the emulsifier is soap.

12. A process according to claim 11 wherein said soap is a potassium soap of hydrogenated fatty acid containing from about 10 to about 22 carbon atoms.

13. A process according to claim 7 wherein molar ratio of fatty acid ester reactant to each esterifiable hydroxy group is from about 1:1 to about 1.2:1.

14. A process according to claim 12 wherein the initial stage of said reaction is carried out under conditions of backmixing until the average degree of esterification of the polyol is from about 20% to about 50% to provide sufficient lower partial polyol polyester to aid in solubilization of the polyol.

15. A process according to claim 14 wherein the initial stage of said reaction is carried out under conditions of back mixing until the average degree of esterification of the polyol is from about 35% to about 45% and then the unreacted polyol is removed.

16. A process according to claim 14 wherein the final stages of the reaction are carried out under plug-flow conditions and after the degree of esterification of said polyol is at least about 35%.

17. A process according to claim 15 wherein any soap that is insoluble in the reaction mixture is removed by filtration after the degree of esterification reaches at least about 60%.

18. A process according to claim 16 wherein the molar ratio of said fatty acid ester reactant to each esterifiable hydroxy group is from about 0.9:1 to about 1.2:1.

19. A process according to claim 15 wherein the temperature in the initial stage of the reaction is from about 130° C. to about 140° C. and in the final stages is from about 90° C. to about 135° C.

20. A process according to claim 15 wherein the pressure is atmospheric or greater in the second stage of the reaction.

21. A process according to claim 19 wherein the mass transfer surface area is increased by sparging with an inert gas.

22. A process according to claim 20 wherein the final stages of the reaction are carried out under plug flow conditions after the degree of esterification is at least about 35%.

23. A process according to claim 14 wherein the pressure on the first stage of the reaction is atmospheric or greater.

24. A process according to claim 14 wherein the unreacted polyol is removed by filtration, centrifugation, or settling.

* * * * *